United States Patent
Kadokawa et al.

(10) Patent No.: US 8,476,208 B2
(45) Date of Patent: Jul. 2, 2013

(54) WATER-SOLUBLE METAL-PROCESSING AGENT, COOLANT, METHOD FOR PREPARATION OF THE COOLANT, METHOD FOR PREVENTION OF MICROBIAL DETERIORATION OF WATER-SOLUBLE METAL-PROCESSING AGENT, AND METAL PROCESSING

(75) Inventors: Toru Kadokawa, Kanagawa (JP); Akio Saito, Kanagawa (JP)

(73) Assignee: Yushiro Chemical Industry Co., Ltd., Tokyo (JP)

( * ) Notice: Subject to any disclaimer, the term of this patent is extended or adjusted under 35 U.S.C. 154(b) by 1014 days.

(21) Appl. No.: 12/443,184

(22) PCT Filed: Sep. 21, 2007

(86) PCT No.: PCT/JP2007/068453
§ 371 (c)(1),
(2), (4) Date: Jun. 5, 2009

(87) PCT Pub. No.: WO2008/038601
PCT Pub. Date: Apr. 3, 2008

(65) Prior Publication Data
US 2010/0093868 A1  Apr. 15, 2010

(30) Foreign Application Priority Data

Sep. 27, 2006  (JP) ................. 2006-263413

(51) Int. Cl.
| | |
|---|---|
| A01N 33/02 | (2006.01) |
| A01N 47/28 | (2006.01) |
| A61K 31/135 | (2006.01) |
| A61K 31/13 | (2006.01) |
| A61K 31/17 | (2006.01) |
| C10L 1/22 | (2006.01) |

(52) U.S. Cl.
USPC ............ 508/558; 514/596; 514/663; 514/656

(58) Field of Classification Search
USPC ........................ 514/646, 596, 663; 508/558
See application file for complete search history.

(56) References Cited

U.S. PATENT DOCUMENTS

| | | | |
|---|---|---|---|
| 3,192,163 A | 6/1965 | Hodge et al. | |
| 4,055,522 A * | 10/1977 | Ashida et al. | 521/113 |
| 4,144,182 A | 3/1979 | Bereuter | |
| 5,969,037 A * | 10/1999 | Hatano et al. | 524/806 |
| 6,235,913 B1 * | 5/2001 | Raths et al. | 554/98 |

FOREIGN PATENT DOCUMENTS

| | | |
|---|---|---|
| EP | 1230971 A1 * | 8/2002 |
| GB | 1 038 521 | 8/1966 |
| JP | 52 152808 | 12/1977 |
| JP | 52-152808 | 12/1977 |
| JP | 60 49094 | 3/1985 |
| JP | 2 228394 | 9/1990 |
| JP | 5 279688 | 10/1993 |
| JP | 9 316482 | 12/1997 |
| JP | 11 50076 | 2/1999 |
| JP | 11 80769 | 3/1999 |
| JP | 2000 17284 | 1/2000 |
| JP | 2003 522216 | 7/2003 |
| JP | 2005 15617 | 1/2005 |
| JP | 2006 348079 | 12/2006 |

OTHER PUBLICATIONS

Japanese Office Action issued on Mar. 27, 2012 in corresponding Japanese Application No. 2006-263413 (with an English Translation).

Office Action issued Sep. 6, 2011, in Chinese Patent Application No. 200780036201.5 with English translation.

Office Action issued Jun. 5, 2012 in Japanese Application No. 2006-263413 (With English Translation).

* cited by examiner

*Primary Examiner* — Benjamin Packard
(74) *Attorney, Agent, or Firm* — Oblon, Spivak, McClelland, Maier & Neustadt, L.L.P.

(57) ABSTRACT

Disclosed are a water-soluble metal-processing agent and a coolant both of which have excellent microbial deterioration resistance and are less likely to go rotten, a method for preparing the agent or the coolant, and a metal processing method. The water-soluble metal-processing agent or the coolant comprises an N,N,N',N'-tetraalkyldiamine compound. The metal processing method is characterized by processing a metal of interest by using the water-soluble metal-processing agent or the coolant.

13 Claims, No Drawings

WATER-SOLUBLE METAL-PROCESSING AGENT, COOLANT, METHOD FOR PREPARATION OF THE COOLANT, METHOD FOR PREVENTION OF MICROBIAL DETERIORATION OF WATER-SOLUBLE METAL-PROCESSING AGENT, AND METAL PROCESSING

FIELD OF THE INVENTION

The present invention relates to a water-soluble metal-processing agent, a coolant, a method for preparation of the coolant, a method for prevention of microbial deterioration of a water-soluble metal-processing agent, and a metal processing.

BACKGROUND ART

Generally, a water-soluble metal-processing agent such as a water-soluble cutting oil agent and a water-soluble grinding oil agent is produced by appropriately mixing components such as a mineral oil, a fatty oil, a fatty acid, a fatty acid ester, an extreme-pressure additive, a surfactant, a defoaming agent, a metal anticorrosive, an antioxidant, an antiseptic agent and an antifungal agent, according to a purpose. The water-soluble metal-processing agent is typically diluted 10 to 100 fold with a diluent such as water, for use. The thus-diluted water-soluble metal-processing agent is called "coolant".

The coolant is required to exhibit excellent performance related to cutting and grinding properties such as improvement in finishing surface accuracy and extension of the lifetime of a tool (hereinafter referred to as "primary performance"), and to a working property and the like (hereinafter referred to as "secondary performance"). The above-mentioned secondary performance includes, for example, good rust resistance, slow deterioration and easy maintenance, harmlessness to the human body, low foaming tendency, and less unpleasant odor.

The water-soluble metal-processing agent and the coolant contain many ingredients which are nourishment sources suitable for a microbial such as a bacterium, a yeast fungus and a filamentous fungus. While the water-soluble metal-processing agent and the coolant are used, a microbial sometimes enters the water-soluble metal-processing agent and the coolant from dilution water, a workpiece, air and the like, and is proliferated therein. The entrance and proliferation of the microbial cause a problem that the water-soluble metal-processing agent and the coolant are putrefied. Development of the rotting of the coolant leads to not only deterioration of work environment but also pipe clogging in the circulation system, reduction in the machining efficiency, and the like. In order to prevent such reduction in the performance due to putrefaction, the water-soluble metal-processing agent and the coolant are supplied and replaced as required. However, if the water-soluble metal-processing agent and the coolant are supplied and replaced with higher frequencies, it is disadvantageous in terms of management of oil agents and cost. Therefore, it is very important to prevent deterioration of the water-soluble metal-processing agent and the coolant due to a microbial.

Hitherto, various kinds of fungicides and antiseptic agents are used to prevent the rotting of the water-soluble metal-processing agent and the coolant. For example, it is well known to add an antiseptic agent and a fungicide such as a formaldehyde-releasing type compound and a phenolic compound to the water-soluble metal-processing agent.

In addition, in order to address the above-mentioned problems, hitherto, a water-soluble metal-processing agent containing a variety of amine compound has been developed. Patent Document 1 discloses a water-soluble metal-processing agent in which dicyclohexylamine and/or cyclohexylamine are/is compounded with m-xylenediamine and/or 1,3-bis(aminomethyl)cyclohexane in a specific ratio. Patent Document 2 discloses a water-soluble metal-processing agent that contains an alkylenediamine having an alkylene group with 2 to 12 carbon atoms. Patent Document 3 discloses a water-soluble metal-processing agent containing N-substituted dialkyldiamine. Patent Document 4 discloses a water-soluble metal-processing agent containing an ethylene oxide adduct or propylene oxide adduct of meta- or ortho-xylenediamine, an ethylene oxide adduct or propylene oxide adduct of 1,3-bis-(aminomethyl)cyclohexylamine, and an ethylene oxide adduct or propylene oxide adduct of 1,4-bis-(aminomethyl)cyclohexylamine.

Since the water-soluble metal-processing agent is typically diluted with water for use, the agent is required to have an excellent rust preventing property for a machine and a workpiece. Particularly, as mentioned above, it is known that the rust preventing property is rapidly lowered as deterioration of the water-soluble metal-processing agent and the coolant due to a microbial is developed. In order to address such a problem, hitherto, a water-soluble metal-processing agent containing an anti-rust agent is used. Patent Document 5 discloses an anti-rust lubricating oil containing an acidic anti-rust agent such as a carboxylic acid and an acid scavenger such as N,N,N',N'-tetraalkyl 1,8-naphthylenediamine.

[Patent Document 1] Japanese Unexamined Patent Application Publication No. JP-A H05-279688

[Patent Document 2] Japanese Unexamined Patent Application Publication No. JP-A H02-228394

[Patent Document 3] Japanese Unexamined Patent Application Publication No. JP-A S60-49094

[Patent Document 4] Japanese Unexamined Patent Application Publication No. JP-A H09-316482

[Patent Document 5] Japanese Unexamined Patent Application Publication No. JP-A 2003-522216

DISCLOSURE OF THE INVENTION

Problems that the Invention is to Solve

Generally, an antiseptic agent has a drawback that it is decomposed or inactivated in a short time and the effect thereof is significantly lowered accordingly. Besides, if a large amount of the antiseptic agent and the fungicide are added, irritation to the human body such as skin irritation becomes intense. The use of the coolant of which irritation to the human body is intense might impose bad influence on the health of the human body (a worker who handles the water-soluble metal-processing agent and the like).

The antiseptic agent and the fungicide also have a drawback that they are not always effective for all microbial. For example, the water-soluble metal-processing agent described in the above-mentioned Patent Document 1 is effective for bacteria to some extent and can suppress the rotting of the water-soluble metal-processing agent to some extent. However, the water-soluble metal-processing agent described in the above-mentioned Patent Document 1 has a drawback that it has a weak antifungal property for a yeast fungus, and therefore cannot achieve a satisfactory result for deterioration of the water-soluble metal-processing agent caused by the yeast fungus. In addition, the water-soluble metal-processing agent of the above-mentioned Patent Document 1 has a drawback that alkalinity thereof is high, and irritation to the human body is still intense.

Furthermore, an amine compound such as an alkanolamine and dicyclohexylamine are used for the water-soluble metal-processing agent for many years. Therefore, microbial gain resistance for these amine compounds. As a result, the rotting prevention effect by these amine compounds has been relatively lowered.

The present invention was accomplished in the light of the above-mentioned circumstances. It is an object of the present invention to provide a water-soluble metal-processing agent and a coolant which are used for metal processing such as cutting, grinding and plastic working, have excellent microbial deterioration resistance, and are capable of sufficiently suppressing the rotting, and a preparation method thereof. It is another object of the present invention to provide a method for preventing a water-soluble metal-processing agent from being deteriorated by a microbial, which allows the agent to have excellent microbial deterioration resistance and sufficiently suppress the rotting. It is still another object of the present invention to provide metal processing such as cutting, grinding and plastic working, using a water-soluble metal-processing agent or a coolant each having excellent microbial deterioration resistance and capable of sufficiently suppressing the rotting.

Means for Solving the Problems

The inventors made extensive study on resistances to putrefaction and deterioration of a water-soluble metal-processing agent caused by microbial proliferation. As a result, the inventors found that a tetraalkyldiamine compound such as N,N,N',N'-tetraalkylalkylenediamine exhibits an extremely good antifungal property for not only a bacterium but also a yeast fungus and a filamentous fungus, and remarkably improves microbial deterioration resistance of a water-soluble metal-processing agent for a long time, and thereby arrived at the present invention.

The present invention is as follows.
[1] A water-soluble metal-processing agent characterized by comprising an N,N,N',N'-tetraalkyldiamine compound.
[2] The water-soluble metal-processing agent according to [1] above, wherein content of the N,N,N',N'-tetraalkyldiamine compound is in the range from 0.5% to 30% by weight based on 100% by weight of the water-soluble metal-processing agent.
[3] The water-soluble metal-processing agent according to [1] above, wherein the N,N,N',N'-tetraalkyldiamine compound is a compound represented by the following general formula (1).

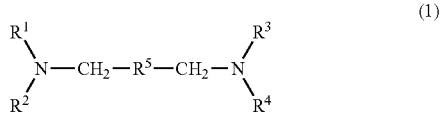

(In the general formula (1), each of $R^1$, $R^2$, $R^3$ and $R^4$ represents an alkyl group having 1 to 12 carbon atoms, and $R^1$, $R^2$, $R^3$ and $R^4$ may be the same group or different groups. In the general formula (1), $R^5$ is a divalent organic group.)
[4] The water-soluble metal-processing agent according to [1] above, wherein the N,N,N',N'-tetraalkyldiamine compound is a compound represented by the following general formula (2).

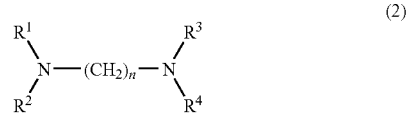

(In the general formula (2), each of $R^1$, $R^2$, $R^3$ and $R^4$ represents an alkyl group having 1 to 12 carbon atoms, and $R^1$, $R^2$, $R^3$ and $R^4$ may be the same group or different groups. In the general formula (2), n is an integer of 3 to 15.)
[5] The water-soluble metal-processing agent according to [1] above, further comprising at least one kind of an anionic surfactant and a nonionic surfactant.
[6] A coolant characterized in that the coolant comprises an N,N,N',N'-tetraalkyldiamine compound, and content of the N,N,N',N'-tetraalkyldiamine compound is 0.01% or more by weight based on 100% by weight of the total amount of the coolant.
[7] The coolant according to [6] above, which is obtained by diluting a water-soluble metal-processing agent containing an N,N,N',N'-tetraalkyldiamine compound with a diluent.
[8] A method for preparation of a coolant characterized by comprising diluting a water-soluble metal-processing agent containing an N,N,N',N'-tetraalkyldiamine compound with a diluent to a content of the N,N,N',N'-tetraalkyldiamine compound of 0.01% or more by weight based on 100% by weight of the total amount of the coolant.
[9] A method for prevention of microbial deterioration of a water-soluble metal-processing agent, characterized by comprising adding an N,N,N',N'-tetraalkyldiamine compound to a water-soluble metal-processing agent.
[10] A metal processing characterized by comprising processing a metal to be processed using a water-soluble metal-processing agent comprising an N,N,N',N'-tetraalkyldiamine compound, or a coolant comprising an N,N,N',N'-tetraalkyldiamine compound, wherein a content of the N,N,N',N'-tetraalkyldiamine compound is 0.01% or more by weight based on 100% by weight of the total amount of the coolant.

Effect of the Invention

The water-soluble metal-processing agent and the coolant of the present invention can be those which have excellent microbial deterioration resistance and are capable of fully suppressing the rotting, by comprising the above-mentioned constituent. The method for preparing a coolant of the present invention can obtain the coolant of the present invention easily exhibiting the above-mentioned function effects, by comprising the above-mentioned constituent. The method for preventing microbial deterioration of a water-soluble metal-processing agent of the present invention can sufficiently suppress the rotting of the water-soluble metal-processing agent for a long time, by comprising the above-mentioned constituent. The metal processing of the present invention facilitates management of oil agents and can be implemented while deterioration of work environment and bad influence on the health of the human body are suppressed, by comprising the above-mentioned constituent.

BEST MODE FOR CARRYING OUT THE INVENTION (1) Water-Soluble Metal-Processing Agent
The water-soluble metal-processing agent of the present invention is characterized by comprising an N,N,N',N'-tetraalkyldiamine compound (hereinafter, referred to simply as "tetraalkyldiamine compound").

The above-mentioned tetraalkyldiamine compound is a compound in which all of the hydrogen atoms of two amino groups contained in a diamine compound are substituted by alkyl groups (N-substituted alkyl groups). The above-mentioned tetraalkyldiamine compound is not particularly limited in specific structure thereof as long as the compound comprises this structure. As the above-mentioned tetraalkyldiamine compound, a tetraalkyldiamine compound other than an N,N,N',N'-tetraalkyl 1,8-naphthylenediamine compound may be used.

The type of the above-mentioned alkyl group is not particularly limited. The number of carbon atoms in the above-mentioned alkyl group is generally in the range from 1 to 12, preferably from 1 to 10, more preferably from 1 to 8, further preferably from 1 to 6, and particularly from 1 to 4. When the number of carbon atoms in the above-mentioned alkyl group is in the above-mentioned range, superior microbial deterioration resistance is exhibited, being favorable. In addition, the above-mentioned alkyl group may be a linear alkyl group, an alkyl group having a side chain, or an alkyl group having a cyclic structure. Furthermore, the above-mentioned alkyl group may contain other atom such as oxygen atom, nitrogen atom, sulfur atom and a halogen atom including chloride atom in a carbon chain. The above-mentioned alkyl group may contain other functional group such as hydroxyl group, thiol group, ether group, carbonyl group and carboxyl group in a carbon chain.

Specific examples of the above-mentioned alkyl group include methyl group, ethyl group, propyl group, butyl group, pentyl group, hexyl group, octyl group, nonyldecyl group, dodecyl group, tetradecyl group, hexadecyl group, octadecyl group, cyclopentyl group, cyclohexyl group, cycloheptyl group, 2-methylcyclohexyl group and the like. Incidentally, four N-substituted alkyl groups contained in the above-mentioned tetraalkyldiamine compound may be all same alkyl groups, or some different kinds of or all different kinds of alkyl groups.

Specific example of the above-mentioned tetraalkyldiamine compound includes the compound represented by the above general formula (1) (hereinafter, referred to simply as "compound (1)"). When the above-mentioned tetraalkyldiamine compound is the above-mentioned compound (1), excellent microbial deterioration resistance is exhibited and the rotting can be sufficiently suppressed, being favorable.

In the above general formula (1), $R^1$, $R^2$, $R^3$ and $R^4$ above are alkyl groups having 1 to 12 carbon atoms. The number of carbon atoms in $R^1$, $R^2$, $R^3$ and $R^4$ above is preferably in the range from 1 to 10, more preferably from 1 to 8, further preferably from 1 to 6, and particularly from 1 to 4. When the above-mentioned number of carbon atoms is in the above-mentioned range, superior microbial deterioration resistance is exhibited, being favorable. In addition, the above-mentioned alkyl group may be a linear alkyl group, an alkyl group having a side chain, or an alkyl group having a cyclic structure. Furthermore, the above-mentioned alkyl group may contain other atom such as oxygen atom, nitrogen atom, sulfur atom and a halogen atom including chloride atom in a carbon chain. The above-mentioned alkyl group may contain other functional group such as hydroxyl group, thiol group, ether group, carbonyl group and carboxyl group in a carbon chain.

Specific examples of $R^1$, $R^2$, $R^3$ and $R^4$ above include methyl group, ethyl group, propyl group, butyl group, pentyl group, hexyl group, octyl group, nonyldecyl group, dodecyl group, tetradecyl group, hexadecyl group, octadecyl group, cyclopentyl group, cyclohexyl group, cycloheptyl group, 2-methylcyclohexyl group and the like. Incidentally, $R^1$, $R^2$, $R^3$ and $R^4$ above may be all same alkyl groups, or some different kinds of or all different kinds of alkyl groups.

The above-mentioned $R^5$ in the above general formula (1) is not particularly limited in specific structure, number of carbon atoms and the like as long as it is a divalent organic group. The above-mentioned $R^5$ is typically a chain alkylene group as in the general formula (2) above. In addition, the above-mentioned $R^5$ may have an alicyclic structure or an aromatic ring structure. Furthermore, the above-mentioned chain alkylene group and the above-mentioned alicyclic structure may have an unsaturated bond in the structure thereof. In addition, the above-mentioned chain alkylene group may be a linear alkylene group or an alkylene group having a side chain.

Example of the compound represented by the above-mentioned general formula (1) includes the compound represented by the above-mentioned general formula (2) (hereinafter, referred to simply as "compound (2)"). When the above-mentioned tetraalkyldiamine compound is the above-mentioned compound (2), excellent microbial deterioration resistance is exhibited and the rotting can be sufficiently suppressed, being favorable. In addition, example of the compound represented by the above-mentioned general formula (1) includes, for example, the compounds represented by the following general formulas (3) and (4).

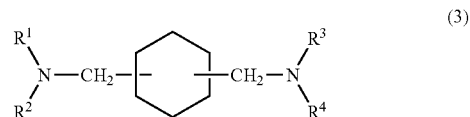

(3)

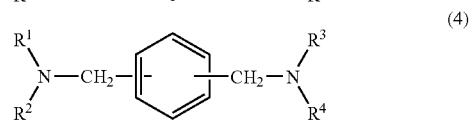

(4)

For details of $R^1$, $R^2$, $R^3$ and $R^4$ of the above-mentioned general formula (2), the explanation for the above-mentioned $R^1$, $R^2$, $R^3$ and $R^4$ of the above-mentioned general formula (2) is applied. In the above-mentioned general formula (2), the above-mentioned n is an integer from 3 to 15, preferably from 4 to 13, and further preferably from 5 to 12. When the above-mentioned n is in the above-mentioned range, excellent microbial deterioration resistance is exhibited and the rotting can be sufficiently suppressed, being favorable.

The content of the above-mentioned tetraalkyldiamine compound is generally in the range from 0.5% to 30% by weight, preferably from 1% to 25% by weight, more preferably from 1% to 20% by weight, further preferably from 1% to 15% by weight, and particularly from 2% to 15% by weight based on 100% by weight of the total amount of the water-soluble metal-processing agent of the present invention. When the above-mentioned tetraalkyldiamine compound is in the above-mentioned range, the water-soluble metal-processing agent of the present invention exhibits excellent microbial deterioration resistance and putrefaction resistance, being favorable.

The water-soluble metal-processing agent of the present invention contains the above-mentioned tetraalkyldiamine compound as an essential component thereof. Additionally, the water-soluble metal-processing agent of the present invention may contain various kinds of optional components therein appropriately as required within a range not to impair the purpose of the present invention, in order to maintain the basic performance as a water-soluble metal-processing agent. The above-mentioned optional component includes a component used in a conventional water-soluble metal-processing agent. The above-mentioned component specifically includes, for example, a surfactant, base oil, an extreme pressure additive, an alcohol, an amine compound (except the above-mentioned tetraalkyldiamine compound), a defoaming agent, a metal anticorrosive, an antiseptic agent and the like. The above-mentioned optional component may be used singly or in combination of two or more types thereof.

The above-mentioned surfactant includes a cationic surfactant, an anionic surfactant and a nonionic surfactant. In the present invention, the above-mentioned surfactant may be used singly or in combination of two or more types thereof. In the water-soluble metal-processing agent of the present invention, at least one kind of the anionic surfactant and nonionic surfactant are preferably used. When the water-soluble metal-processing agent of the present invention additionally contains at least one kind of the anionic surfactant and nonionic surfactant, the agent further has excellent microbial deterioration resistance and the rotting can be sufficiently suppressed.

Examples of the above-mentioned anionic surfactant include a salt of a fatty acid and an amine compound, a metal salt of a fatty acid, a petroleum sulfonate and the like. As the above-mentioned fatty acid, a fatty acid having 6 to 36 carbon atoms which is used for an ordinary aqueous metal-processing agent is used. The above-mentioned fatty acid may be a monocarboxylic acid or a dicarboxylic acid. Examples of the above-mentioned fatty acid include caproic acid, caprylic acid, nonane acid, lauric acid, coconut oil fatty acid, oleic acid, erucic acid, ricinoleic acid, rapeseed oil fatty acid, ricinoleic acid condensate, a C21-aliphatic dicarboxylic acid, adipic acid, sebacic acid, dodecanoic acid and dodecane diacid. Among these, coconut oil fatty acid, rapeseed oil fatty acid, oleic acid, ricinoleic acid, erucic acid, ricinoleic acid condensate, a C21-aliphatic dicarboxylic acid, adipic acid, dodecanoic acid and dodecane diacid are preferably used.

Examples of the above-mentioned metal salt include an alkali metal salt such as a sodium salt and a potassium salt. Therefore, the above-mentioned metal salt of a fatty acid specifically includes, for example, an alkali metal salt such as a sodium salt and a potassium salt of each of the fatty acids which are exemplified above.

Examples of the above-mentioned nonionic surfactant specifically include a polyoxyalkylene alkyl ether such as polyoxyethylene alkylether and polyoxyethylene polyoxypropylene alkylether, a polyethylene glycol-polypropylene glycol block polymer, coconut oil fatty acid diethanolamide, oleic acid diethanolamide and the like.

In the water-soluble metal-processing agent of the present invention, the content of the above-mentioned surfactant can be set in various ranges as needed. The content of the above-mentioned surfactant is generally in the range from 1% to 40% by weight, preferably from 3% to 35% by weight, more preferably from 5% to 35% by weight, further preferably from 8% to 30% by weight, and particularly from 10% to 30% by weight based on 100% by weight of the total amount of the water-soluble metal-processing agent of the present invention. When the content of the surfactant is in the above-mentioned range, the water-soluble metal-processing agent of the present invention exhibits excellent microbial deterioration resistance, being favorable.

In the water-soluble metal-processing agent of the present invention, in the case where an anionic surfactant and a nonionic surfactant are used in combination, the content ratio between can be set in various ranges as needed. When the total content of the above-mentioned anionic surfactant and the above-mentioned nonionic surfactant is made to 100% by weight, the content of the above-mentioned anionic surfactant is generally in the range from 30% to 95% by weight, preferably from 40% to 95% by weight, more preferably from 50% to 90% by weight, further preferably from 60% to 90% by weight, and particularly from 70% to 90% by weight. When the content of the anionic surfactant is in the above-mentioned range, the water-soluble metal-processing agent of the present invention exhibits excellent microbial deterioration resistance, being favorable.

In the water-soluble metal-processing agent of the present invention, the content ratio between the above-mentioned surfactant and the above-mentioned tetraalkyldiamine compound can be set in various ranges as needed. When the total content of the above-mentioned surfactant and the above-mentioned tetraalkyldiamine compound is made to 100% by weight, the content of the above-mentioned tetraalkyldiamine compound is generally in the range from 1% to 40% by weight, preferably from 1% to 30% by weight, more preferably from 1% to 25% by weight, further preferably from 2% to 20% by weight, and particularly from 3% to 20% by weight. When the content of the tetraalkyldiamine compound is in the above-mentioned range, the water-soluble metal-processing agent of the present invention exhibits excellent microbial deterioration resistance, being favorable.

The above-mentioned amine compound may be any of an aliphatic amine, an alicyclic amine and an aromatic amine. In addition, the above-mentioned amine compound may be an amine compound having other functional group such as alkanolamine. Furthermore, an amino group contained in the above-mentioned amine compound may be any of a primary amino group, a secondary amino group, and a tertiary amino group. The number of amino groups contained in the above-mentioned amine compound is not particularly limited. The amine compound may be any of a monoamine compound, a diamine compound, a triamine compound, and a tetraamine compound. In the present invention, the above-mentioned amine compound is preferably used an amine compound having carbon atoms of usually from 2 to 36, preferably from 2 to 20, and more preferably from 2 to 15. The amine compound may be used singly or in combination of two or more types thereof.

Examples of the above-mentioned alkanolamine include monoethanolamine, diethanolamine, triethanolamine, monoisopropanolamine, diisopropanolamine, triisopropanolamine, N,N-dimethylethanolamine, N,N-diethyethanolamine, n-butylethanolamine, 2-amino-2-methyl-1-propanol, 2-amino-1-butanol, N-aminoethyethanolamine and the like. Among these, diethanolamine, triethanolamine and monoisopropanolamine are preferably used. In addition, examples of the above-mentioned aliphatic amine include octylamine, decylamine, laurylamine, oleylamine, hexamethylenediamine and the like. Further, examples of the alicyclic amine include cyclohexylamine, dicyclohexylamine and the like. Moreover, examples of the above-mentioned aromatic amine include benzylamine, dibenzylamine and the like.

In the water-soluble metal-processing agent of the present invention, the content of the above-mentioned amine compound is preferably not more than 30% by weight, more preferably in the range from 0.01% to 30% by weight, further preferably from 0.1% to 25% by weight, particularly from 1% to 20% by weight based on 100% by weight of the total amount of the water-soluble metal-processing agent of the present invention. When the content of the above-mentioned amine compound is in the above-mentioned range, excellent microbial deterioration resistance and corrosion resistance are exhibited, being favorable.

In the water-soluble metal-processing agent of the present invention, the content ratio between the above-mentioned amino compound and the above-mentioned tetraalkyldiamine compound can be set in various ranges as needed.

When the total content of the above-mentioned amine compound and the above-mentioned tetraalkyldiamine compound is made to 100% by weight, the content of the above-mentioned amine compound is generally in the range of 1% to 95% by weight, preferably from 10% to 95% by weight, more preferably from 30% to 90% by weight, further preferably from 50% to 85% by weight, and particularly from 60% to 80% by weight. When the content of the amine compound is in the above-mentioned range, the water-soluble metal-processing agent of the present invention exhibits excellent microbial deterioration resistance, being favorable.

In addition, the water-soluble metal-processing agent of the present invention can have a constitution in which a primary amine compound such as a primary diamine compound is not contained therein, or a constitution in which a primary amine compound is contained in such an amount that the primary amine compound does not strengthen irritation to the human body such as skin irritation (for example, when the whole amount of the water-soluble metal-processing agent of the present invention is made to 100% by weight, the content of the primary amine compound therein is more than 0% by weight and not more than 1.0% by weight, preferably 0.5% or less by weight, more preferably 0.3% or less by weight, and further preferably 0.1% or less by weight). Unless the water-soluble metal-processing agent of the present invention contain such a primary amine compound, excellent microbial deterioration resistance is exhibited and the agent can weaken irritation to the human body caused by the water-soluble metal-processing agent and the coolant, being favorable.

The above-mentioned alcohol is preferably used an alcohol having 12 to 18 carbon atoms. Specific structure of the above-mentioned alcohol is not particularly limited. The above-mentioned alcohol may be any of primary, secondary and tertiary alcohols. In addition, the alcohol may be a linear alcohol or an alcohol having a side chain. Furthermore, number of hydroxyl groups of the above-mentioned alcohol is not particularly limited. The above-mentioned alcohol may be any of a monoalcohol, a dialcohol and a trialcohol. Examples of the above-mentioned alcohol include n-tridecanol, iso-tridecanol, n-pentadecanol, iso-pentadecanol and the like. The above-mentioned alcohol may be used singly or in combination of two or more types thereof.

Specific examples of the above-mentioned base oil include a mineral oil, a synthetic ester, animal and plant oils/fats and the like. The water-soluble metal-processing agent of the present invention can have a further improved lubricating property by containing the above-mentioned base oil. In the water-soluble metal-processing agent of the present invention, the above-mentioned base oil may be used singly or in combination of two or more types thereof.

The above-mentioned mineral oil represents a component obtained by refining and distilling petroleum. As the above-mentioned mineral oil, a mineral oil subjected to a process such as hydrogenation and modification can be used. Specific examples of the above-mentioned mineral oil include a spindle oil, a machine oil and the like. The physical properties of the above-mentioned mineral oil are not particularly limited. For example, a kinematic viscosity (40° C.) of the above-mentioned mineral oil is generally 0.1 mm$^2$/s or higher, preferably in the range from 0.5 to 150 mm$^2$/s, more preferably from 1 to 60 mm$^2$/s, and further preferably from 5 to 60 mm$^2$/s. In addition, an aniline point of the above-mentioned mineral oil is generally in the range of 35° C. to 120° C., preferably from 40° C. to 100° C., more preferably from 45° C. to 100° C., and further preferably from 50° C. to 90° C. The above-mentioned mineral oil may be used singly or in combination of two or more types thereof.

As the above-mentioned synthetic ester, an ester of a carboxylic acid having usually 10 to 30 carbon atoms, preferably 12 to 28 carbon atoms, and more preferably 15 to 25 carbon atoms, and an alcohol having usually 1 to 30 carbon atoms, preferably 1 to 25 carbon atoms, and more preferably 1 to 20 carbon atoms is used. The above-mentioned alcohol may be any of primary, secondary and tertiary alcohols. In addition, the above-mentioned alcohol may be any of monoalcohol, dialcohol, trialcohol and tetraalcohol. Specific examples of the synthetic ester include methyl oleate, 2-ethylhexyl oleate, neopentylglycol dioleate, trimethylolpropane trioleate, pentaerythritol tetraoleate and the like. Among these, 2-ethylhexyl oleate, neopentylglycol dioleate and trimethylolpropane trioleate are preferably used. The above-mentioned synthetic ester may be used singly or in combination of two or more types thereof.

Examples of the above-mentioned animal and plant oils/fats include an animal oil/fat such as lard, beef tallow and fish oil, and a plant oil/fat such as rapeseed oil, soybean oil and palm oil. In addition, as the above-mentioned animal and plant oils/fats, a hydrogenated product of the above-mentioned animal and plant oils/fats can also be used. The above-mentioned animal and plant oils/fats may be used singly or in combination of two or more types thereof.

The content of the above-mentioned base oil is generally not more than 80% by weight, preferably in the range from 0.1% to 80% by weight, more preferably from 1% to 75% by weight, further preferably from 5% to 70% by weight, furthermore preferably from 10% to 60% by weight, and particularly from 20% to 60% by weight based on 100% by weight of the total amount of the water-soluble metal-processing agent of the present invention. When the content of the above-mentioned base oil is in the above-mentioned range, the water-soluble metal-processing agent of the present invention exhibits excellent microbial deterioration resistance and an excellent lubricating property, being favorable.

Additionally, in the water-soluble metal-processing agent of the present invention, the content ratio between the above-mentioned base oil and the above-mentioned tetraalkyldiamine compound can be set in various ranges as needed. When the total content of the above-mentioned base oil and the above-mentioned tetraalkyldiamine compound is made to 100% by weight, the content of the above-mentioned base oil is generally in the range from 50% to 99% by weight, preferably from 60% to 98% by weight, more preferably from 70% to 95% by weight, and particularly from 80% to 95% by weight. When the ratio between the above-mentioned base oil and the above-mentioned tetraalkyldiamine compound is in the above-mentioned range, the water-soluble metal-processing agent of the present invention exhibits excellent microbial deterioration resistance and an excellent lubricating property, being favorable.

Water is typically blended in the water-soluble metal-processing agent of the present invention. The blending amount of the water is not particularly limited. The blending amount of the water is generally in the range from 1% to 99% by weight, preferably from 5% to 90% by weight, more preferably from 5% to 80% by weight, further preferably from 7% to 70% by weight, particularly from 10% to 50% by weight based on 100% by weight of the water-soluble metal-processing agent of the present invention.

The water-soluble metal-processing agent of the present invention can be used as is. Alternatively, at the time of use, the water-soluble metal-processing agent of the present invention can be further diluted with a diluent such as water for use.

(2) Coolant and Preparation Method Thereof

The coolant of the present invention is characterized in that it contains the above-mentioned tetraalkyldiamine compound, and that the content of the above-mentioned tetraalkyldiamine compound is at least 0.01% by weight based on 100% by weight of the total amount of the coolant. In addition, the method for preparation of a coolant of the present invention is characterized by comprising diluting a water-soluble metal-processing agent with a diluent to a content of the above-mentioned tetraalkyldiamine compound of 0.01% or more by weight based on 100% by weight of the total amount of the coolant.

The content of the above-mentioned tetraalkyldiamine compound is generally 0.01% or more by weight, preferably from 0.01% to 10% by weight, more preferably from 0.01% to 7% by weight, further preferably from 0.01% to 5% by weight, and particularly from 0.05% to 5% by weight based on 100% by weight of the total amount of the coolant. When the content of the above-mentioned tetraalkyldiamine compound is in the above-mentioned range, the coolant exhibits an excellent effect of improving putrefaction resistance and becomes economical, being favorable.

The method for obtaining the coolant of the present invention is not particularly limited. The coolant of the present invention can generally be obtained by diluting the water-soluble metal-processing agent of the present invention with a diluent.

The type of the above-mentioned diluent is not particularly limited. As the above-mentioned diluent, water is typically used. Additionally, in the case where the coolant of the present invention is obtained by diluting the water-soluble metal-processing agent of the present invention, the dilution rate thereof is not particularly limited. The above-mentioned dilution rate is generally in the range from 1.5 to 100 fold, preferably from 2 to 70 fold, more preferably from 5 to 50 fold, and particularly from 10 to 50 fold.

(3) Method for Preventing Microbial Deterioration of Water-Soluble Metal-Processing Agent The method for prevention of microbial deterioration of a water-soluble metal-processing agent of the present invention is characterized by comprising adding an N,N,N',N'-tetraalkyldiamine compound to a water-soluble metal-processing agent The kind and composition of the above-mentioned water-soluble metal-processing agent is not particularly limited. The above-mentioned water-soluble metal-processing agent usually contains water. In addition, examples of the components contained in the above-mentioned water-soluble metal-processing agent include an optional component in the above-mentioned water-soluble metal-processing agent, that is, for example, a surfactant, base oil, an extreme pressure additive, an alcohol, an defoaming agent, a metal anticorrosive, an antiseptic agent and the like. The optional component may be used singly or in combination of two or more types thereof. Incidentally, for the above-mentioned optional components, the explanation fully given in the section of the water-soluble metal-processing agent of the present invention is also applied. Further, in the method for preventing microbial deterioration of the water-soluble metal-processing agent of the present invention, the above-mentioned "water-soluble metal-processing agent" is a concept which includes the "coolant" obtained after the water-soluble metal-processing agent is diluted with a diluent such as water.

For details of the above-mentioned N,N,N',N'-tetraalkyldiamine compound, the explanation fully given in the section of the water-soluble metal-processing agent of the present invention is also applied. In addition, a method for adding the above-mentioned N,N,N',N'-tetraalkyldiamine compound is not particularly limited. Furthermore, a formulating amount of the above-mentioned N,N,N',N'-tetraalkyldiamine compound can be appropriately set as required. The above-mentioned N,N,N',N'-tetraalkyldiamine compound can be so added that, in 100% by weight of the water-soluble metal-processing agent (the concept thereof includes the "coolant"), the content of the above-mentioned tetraalkyldiamine compound is not less than 0.01% by weight, preferably in the range from 0.01% to 10% by weight, more preferably from 0.01% to 7% by weight, further preferably from 0.01% to 5% by weight, and particularly from 0.05% to 5% by weight. When the formulating amount is such amount, the water-soluble metal-processing agent has an excellent effect of improving putrefaction resistance and becomes economical, being favorable.

(4) Metal Processing

The metal processing of the present invention is characterized by comprising processing a metal to be processed using a water-soluble metal-processing agent of the present invention or the coolant of the present invention.

The metal processing of the present invention is not particularly limited with regard to the specific details thereof, as long as it is a method for processing metal. Examples of the above-mentioned metal processing include cutting, grinding, plastic working and the like. Additionally, in the above-mentioned metal processing a method for supplying the above-mentioned water-soluble metal-processing agent or the above-mentioned coolant is not particularly limited. The method includes, for example, a method for feeding through a nozzle using a circulation pump, manual oil feeding (brush application, lubrication, etc.), spray oil feeding and the like.

The specific details of the above-mentioned metal to be processed are not particularly limited. For example, the materials of the above-mentioned metal to be processed typically are a steel and an iron alloy, such as iron, carbon steel and stainless steel, and other than these, the material may also be a nonferrous metal and an alloy thereof, such as inconel, titanium, a titanium alloy, aluminum, an aluminum alloy, magnesium, a magnesium alloy, copper and a copper alloy. The shape of the above-mentioned metal to be processed is not particularly limited, either and the shape thereof includes, for example, a rod-like shape, a block-like shape and the like.

EXAMPLES

Hereinafter, the present invention is specifically described using Examples.

(1) Preparation of Water-Soluble Metal-Processing Agent

Components shown in Table 1 were blended at a ratio shown in Table 1 to prepare water-soluble metal-processing agents of Experimental Examples 1 to 8. A unit showing a composition of Table 1 is % by weight. In addition, details of the components described in Table 1 are follows.

Mineral oil: Spindle oil (dynamic viscosity; 8 mm$^2$/s (40° C.), aniline point; 59° C.)

Synthetic ester: 2-Ethylhexyl oleate

Ether carboxylic acid: Polyoxyethylene oleil ether carboxylic acid

Nonionic surfactant: Mixture of polyoxyalkylene alkyl ethers (C15 and C16)

Antiseptic agent: Hexahydro-tris(2-hydroxyethyl)-S-triazine

TABLE 1

| | Experimental Examples | | | | | | | |
|---|---|---|---|---|---|---|---|---|
| | 1 | 2 | 3 | 4 | 5 | 6 | 7 | 8 |
| Mineral oil | 30 | 30 | 30 | 30 | 30 | 30 | 30 | 30 |
| Synthetic ester | 10 | 10 | 10 | 10 | 10 | 10 | 10 | 10 |
| Dodecanedioic acid | 2 | 2 | 2 | 2 | 2 | 2 | 2 | 2 |
| C21 aliphatic dicarboxylic acid | 3 | 3 | 3 | 3 | 3 | 3 | 3 | 3 |
| Ricinoleic acid condensate | 10 | 10 | 10 | 10 | 10 | 10 | 10 | 10 |
| Oleic acid | 6 | 6 | 6 | 6 | 6 | 6 | 6 | 6 |
| Ricinoleic acid | 2 | 2 | 2 | 2 | 2 | 2 | 2 | 2 |
| Isononaoic acid | 1 | 1 | 1 | 1 | 1 | 1 | 1 | 1 |
| Ether carboxylic acid | 1 | 1 | 1 | 1 | 1 | 1 | 1 | 1 |
| Nonionic surfactant A | 4 | 4 | 4 | 4 | 4 | 4 | 4 | 4 |
| Monoisopropanol amine | 4 | 4 | 4 | 4 | 4 | 4 | 4 | 4 |
| Dietheanol amine | 3 | 3 | 3 | 3 | 3 | 3 | 3 | 3 |
| 2-Amino-2-methylpropanol | 4 | 4 | 4 | 4 | 4 | 4 | 4 | 4 |
| Water | 16 | 16 | 16 | 16 | 16 | 16 | 16 | 19 |
| N,N,N',N'-tetramethyl-hexamethylenediamine | 4 | | | | | | | |
| N,N,N',N'-tetraethyl-hexamethylenediamine | | 4 | | | | | | |
| N,N,N',N'-tetramethyl-1,8-diaminooctane | | | 4 | | | | | |
| N,N,N',N'-tetramethyl-1,10-diaminodecane | | | | 4 | | | | |
| N,N-dibutylaminopropylamine | | | | | 4 | | | |
| Hexamethylenediamine | | | | | | 4 | | |
| Dicyclohexylamine | | | | | | | 4 | |
| Antiseptic agent A | | | | | | | | 1 |
| Total | 100 | 100 | 100 | 100 | 100 | 100 | 100 | 100 |

(2) Microbial Deterioration Test

Each of the water-soluble metal-processing agents of Experimental Examples 1 to 8 shown in Table 1 was diluted with tap water to prepare a coolant. This coolant was used as a sample of a microbial deterioration test. A concentration of the water-soluble metal-processing agent in this coolant was 3.3% by weight.

2,000 g of the sample was placed into a water tank having a volume of 5 L. Then, 200 g of a cast metal swarf and 100 g of a lubricant (trade name "Vactora No2SLC" manufactured by Mobil Corporation) were added to the sample, and the mixture was circulated with a pump. Thereafter, as a seed bacterium, a rotten emulsion (pH 7.6, live bacteria number $10^7$ or more/ml, yeast fungi number $10^3$/ml, filamentous fungi number $10^2$/ml) was added to the above-mentioned sample. The above-mentioned emulsion was added at 60 ml on the first day, at 20 ml after one day, at 20 ml after two days, and at 20 ml after seven days and, thereafter, each 20 ml was added every one week. During the test, evaporated moisture was supplemented by adding tap water every day.

Every one week from test initiation, a potion of the each sample was taken. Then, according to the method described below, the number of live bacteria in the each sample taken was measured and, at the same time, a pH and the presence of an odor were measured. The results are shown in Tables 2 and 3.

(2-1) Measurement of the Number of Live Bacteria, the Number of Yeast Fungi and the Number of Filamentous Fungi The number of live bacteria was measured using a normal agar medium by the plate counting method. The number of yeast fungi and the number of filamentous fungi were measured using a potato dextrose agar medium in accordance with the plate counting method.

(2-2) Assessment of Odor

For assessing an odor, an intensity of an order was measured based on the following 3-stage assessment criteria.

○: No putrid odor
Δ: Slight putrid odor
×: Putrid odor (2-3) Assessment of Rust Preventing Property Rust preventing property was assessed by the cast metal swarf method. Specifically, about 15 g of dry-cut cast metal swarf (FC25, 8 to 12 mesh) was taken in a petri dish (internal diameter 60 mm). Then, 25 ml of the sample was added to the petri dish, and was sufficiently shaken before being allowed to stand for about 4 minutes. Thereafter, the sample was removed by a decanting method, and a rust generated on the petri dish was observed over time.

◉: No rust generation
○: Generation of a few points of rust
Δ: Generation of approximately a dozen of points of rust
×: Generation of ⅓ or more of surface of rust

TABLE 2

| | | Before addition of seed bacterium | 1st week | 2nd week | 3rd week | 4th week |
|---|---|---|---|---|---|---|
| Experimental Examples | 1 pH | 9.6 | 9.1 | 9.1 | 9.1 | 9.0 |
| | Odor | ○ | ○ | ○ | ○ | ○ |
| | Rust preventing property 6 hr | ◉ | ◉ | ◉ | ◉ | ◉ |
| | Rust preventing property 24 hr | ◉ | ◉ | ◉ | ◉ | ◉ |
| | Number of live bacteria (cells/ml) | 0 | <$10^3$ | <$10^3$ | <$10^3$ | <$10^3$ |
| | Number of yeast fungi (cells/ml) | 0 | N | N | N | N |
| | Number of filamentous fungi (cells/ml) | 0 | N | N | N | N |
| | 2 pH | 9.6 | 9.2 | 9.1 | 9.1 | 9.1 |
| | Odor | ○ | ○ | ○ | ○ | ○ |

TABLE 2-continued

| | | Before addition of seed bacterium | 1st week | 2nd week | 3rd week | 4th week |
|---|---|---|---|---|---|---|
| | Rust preventing property 6 hr | ◎ | ◎ | ◎ | ◎ | ◎ |
| | Rust preventing property 24 hr | ◎ | ◎ | ◎ | ◎ | ◎ |
| | Number of live bacteria (cells/ml) | 0 | <$10^3$ | <$10^3$ | <$10^3$ | <$10^3$ |
| | Number of yeast fungi (cells/ml) | 0 | N | N | N | N |
| | Number of filamentous fungi (cells/ml) | 0 | N | N | N | N |
| 3 | pH | 9.5 | 9.1 | 9.0 | 9.0 | 9.0 |
| | Odor | ○ | ○ | ○ | ○ | ○ |
| | Rust preventing property 6 hr | ◎ | ◎ | ◎ | ◎ | ◎ |
| | Rust preventing property 24 hr | ◎ | ◎ | ◎ | ◎ | ◎ |
| | Number of live bacteria (cells/ml) | 0 | <$10^3$ | <$10^3$ | <$10^3$ | <$10^3$ |
| | Number of yeast fungi (cells/ml) | 0 | N | N | N | N |
| | Number of filamentous fungi (cells/ml) | 0 | N | N | N | N |
| 4 | pH | 9.4 | 9.1 | 9.0 | 9.0 | 9.0 |
| | Odor | ○ | ○ | ○ | ○ | ○ |
| | Rust preventing property 6 hr | ◎ | ◎ | ◎ | ◎ | ◎ |
| | Rust preventing property 24 hr | ◎ | ◎ | ◎ | ◎ | ◎ |
| | Number of live bacteria (cells/ml) | 0 | <$10^3$ | <$10^3$ | <$10^3$ | <$10^3$ |
| | Number of yeast fungi (cells/ml) | 0 | N | N | N | N |
| | Number of filamentous fungi (cells/ml) | 0 | N | N | N | N |

(3) Note) N: undetected

TABLE 3

| | | | Before addition of seed bacterium | 1st week | 2nd week | 3rd week | 4th week |
|---|---|---|---|---|---|---|---|
| Experimental Examples | 5 | pH | 9.4 | 9.0 | 9.0 | 8.8 | 8.7 |
| | | Odor | ○ | ○ | ○ | Δ | X |
| | | Rust preventing property 6 hr | ◎ | ◎ | ◎ | ◎ | ○ |
| | | Rust preventing property 24 hr | ◎ | ◎ | ◎ | ◎ | ○ |
| | | Number of live bacteria (cells/ml) | 0 | <$10^3$ | <$10^3$ | $10^4$ | $10^7$ |
| | | Number of yeast fungi (cells/ml) | 0 | $10^2$ | $10^3$ | $10^4$ | $10^4$ |
| | | Number of filamentous fungi (cells/ml) | 0 | N | N | N | N |
| | 6 | pH | 9.8 | 9.0 | 9.0 | 8.8 | 8.7 |
| | | Odor | ○ | ○ | ○ | ○ | Δ |
| | | Rust preventing property 6 hr | ◎ | ◎ | ◎ | ◎ | ○ |
| | | Rust preventing property 24 hr | ◎ | ◎ | ◎ | ◎ | ○ |
| | | Number of live bacteria (cells/ml) | 0 | <$10^3$ | <$10^3$ | <$10^3$ | $10^4$ |
| | | Number of yeast fungi (cells/ml) | 0 | N | N | $10^2$ | $10^4$ |
| | | Number of filamentous fungi (cells/ml) | 0 | N | N | 10 | 10 |
| | 7 | pH | 9.2 | 8.9 | 9.0 | 8.9 | 8.6 |
| | | Odor | ○ | ○ | ○ | Δ | X |
| | | Rust preventing property 6 hr | ◎ | ◎ | ◎ | ◎ | ○ |
| | | Rust preventing property 24 hr | ◎ | ◎ | ◎ | ◎ | ○ |
| | | Number of live bacteria (cells/ml) | 0 | <$10^3$ | <$10^3$ | $10^4$ | $10^5$ |
| | | Number of yeast fungi (cells/ml) | 0 | $10^2$ | $10^4$ | $10^4$ | $10^4$ |
| | | Number of filamentous fungi (cells/ml) | 0 | N | N | N | N |
| | 8 | pH | 9.2 | 8.7 | 8.5 | | *1 |
| | | Odor | ○ | Δ | X | | |
| | | Rust preventing property 6 hr | ◎ | ◎ | ○ | | |
| | | Rust preventing property 24 hr | ◎ | ○ | X | | |
| | | Number of live bacteria (cells/ml) | 0 | $10^4$ | >$10^7$ | | |
| | | Number of yeast fungi (cells/ml) | 0 | $10^2$ | $10^4$ | | |
| | | Number of filamentous fungi (cells/ml) | 0 | 10 | $10^2$ | | |

Note)
N: undetected
*1; Experiment aborted (3) Assessment Results

As is clear from Table 2, in Experimental Examples 1 to 4 included in the present invention, reduction in a pH was small and a pH was maintained at 9.0 or higher even after four weeks passed. Additionally, in Experimental Examples 1 to 4, the number of live bacteria was less than $10^3$/ml, and even after four weeks passed, the yeast fungi and the filamentous fungi were undetected. Further, in Experimental Examples 1 to 4, 24 hours-rust did not occur even after four weeks passed.

On the other hand, according to results in Table 3, in Experimental Example 5 (using N, N-dialkyldiamine compound), Experimental Example 6 (using alkylenediamine (N-unsubstituted amine)), Experimental Example 7 (using secondary monoamine compound), and Experimental Example 8 (using non-amine-based antiseptic agent), reduction in a pH was greater as compared with Experimental Examples 1 to 4, and a pH was reduced to less than 9.0 at the time when three weeks passed. In addition, a putrid odor was generated at the time when three weeks passed in Experimental Examples 5 and 7, a putrid odor was generated at the time when four weeks passed in Experimental Example 6, and a putrid odor was generated at the time when one week passed in Experimental Example 8, respectively. Further, in Experimental Examples 5 to 7, rust was generated after four weeks passed and, in Experimental Example 8, rust was already generated at the time when one week passed.

Further, as is clear from Table 3, in Experimental Example 5, the number of live bacteria remarkably increased to $10^4$/ml at the time when three weeks passed, and the number of yeast fungi remarkably increased to $10^2$/ml at when one week passed. In Experimental Example 6, the number of live bacteria was less than $10^3$/ml at the time when three weeks passed, but increased to $10^4$/ml at the time when four weeks passed. In Experimental Example 6, the number of yeast fungi and the number of filamentous fungi increased to $10^2$/ml and 10/ml, respectively, at the time when three weeks passed. Additionally, in Experimental Example 7, the number of live bacteria increased to $10^4$/ml at the time when three weeks passed, and the number of yeast fungi increased to $10^2$/ml at the time when one week passed. In Experimental Example 8, the number of live bacteria increased to $10^4$/ml, the number of yeast fungi increased to $10^2$/ml, and the number of filamentous fungi increased to 10/ml at the time of one week passed. Note that in Experimental Example 8, the number of live bacteria became $10^7$/ml or more at the time when two weeks passed, and a coolant thus became rotten. Therefore, in Experimental Example 8, the experiment was aborted at the time when two weeks passed.

From the foregoing, it has been found that the water-soluble metal-processing agent and the coolant of the present invention have excellent anti-microbial deterioration on not only bacteria, but also yeast fungi and filamentous fungi. Additionally, it has been found that the water-soluble processing agent and the coolant of the present invention can exert anti-microbial deterioration over a long period of time and prevent the rotting. Further, it has been found that since the water-soluble metal-processing agent and the coolant of the present invention do not contain a primary diamine compound where skin irritation is strong, they are weak in irritation to a human body.

The present invention is not limited to the above specific Examples. Embodiments of the present invention can be variously changed in the scope of the present invention, depending on the purpose and application.

[Industrial Applicability]

The water-soluble metal-processing agent and the coolant of the present invention are excellent in anti-microbial deterioration, and can sufficiently prevent the rotting, as compared with the conventional water-soluble metal-processing agent and coolant. The present invention can be effectively utilized for metal processing such as cutting, grinding and plastic working.

The invention claimed is:

1. A water-soluble metal-processing composition comprising an N,N,N',N'-tetraalkyldiamine compound represented by the following formula (1), and dodecanedioic acid,

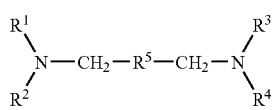
(1)

wherein each of $R^1$, $R^2$, $R^3$ and $R^4$ represents an alkyl group having 1 to 12 carbon atoms, and $R^1$, $R^2$, $R^3$ and $R^4$ may be the same group or different groups and wherein $R^5$ is a divalent organic group.

2. The water-soluble metal-processing agent according to claim 1, wherein said N,N,N',N'-tetraalkyldiamine compound is present in the range from 0.5% to 30% by weight based on 100% by weight of said water-soluble metal-processing agent.

3. The water-soluble metal-processing agent according to claim 1, wherein said N,N,N',N'-tetraalkyldiamine compound is at least one compound selected from the group consisting of compounds represented by the following formulae (2) to (4).

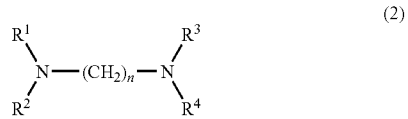
(2)

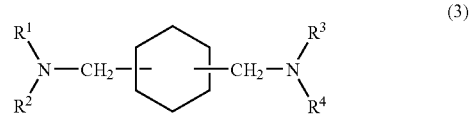
(3)

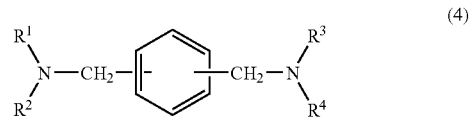
(4)

wherein each of $R^1$, $R^2$, $R^3$ and $R^4$ represents an alkyl group having 1 to 12 carbon atoms, and $R^1$, $R^2$, $R^3$ and $R^4$ may be the same group or different groups and wherein n is an integer of 3 to 15.

4. The water-soluble metal-processing agent according to claim 1, further comprising at least one kind of an anionic surfactant and a nonionic surfactant.

5. A coolant, comprising:
dodecanedioic acid and an N,N,N',N'-tetraalkyldiamine compound represented by the following formula (1), which is present in an amount of 0.01% or more by weight based on 100% by weight of the total amount of said coolant

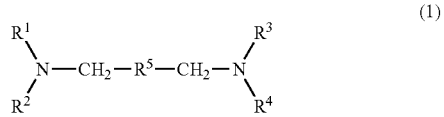
(1)

wherein each of $R^1$, $R^2$, $R^3$ and $R^4$ represents an alkyl group having 1 to 12 carbon atoms, and $R^1$, $R^2$, $R^3$ and $R^4$ may be the same group or different groups and wherein $R^5$ is a divalent organic group.

6. The coolant according to claim 5, which is obtained by diluting the water-soluble metal-processing agent according to claim 1 with a diluent.

7. The coolant according to claim 5, wherein said N,N,N', N'-tetraalkyldiamine compound is at least one compound selected from the group consisting of compounds represented by the following formulae (2) to (4).

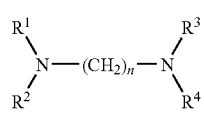
(2)

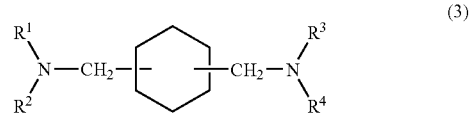
(3)

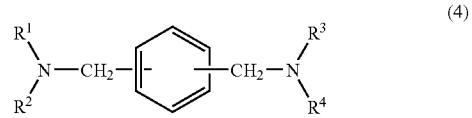
(4)

wherein each of $R^1$, $R^2$, $R^3$ and $R^4$ represents an alkyl group having 1 to 12 carbon atoms, and $R^1$, $R^2$, $R^3$ and $R^4$ may be the same group or different groups and wherein n is an integer of 3 to 15.

8. A method for the prevention of microbial deterioration of a water-soluble metal-processing agent, comprising:
adding an N,N,N',N'-tetraalkyldiamine compound represented by the following formula (1) and dodecanedioic acid to a water-soluble metal-processing agent

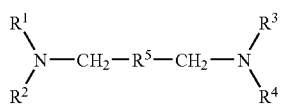

(1)

wherein each of $R^1$, $R^2$, $R^3$ and $R^4$ represents an alkyl group having 1 to 12 carbon atoms, and $R^1$, $R^2$, $R^3$ and $R^4$ may be the same group or different groups and wherein $R^5$ is a divalent organic group.

9. A method of processing metal, comprising:
processing a metal with the water-soluble metal-processing agent according to claim 1.

10. The method for prevention of microbial deterioration of a water-soluble metal-processing agent according to claim 8, wherein said N,N,N',N'-tetraalkyldiamine compound is at least one compound selected from the group consisting of compounds represented by the following formulae (2) to (4).

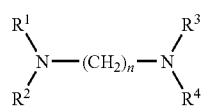

(2)

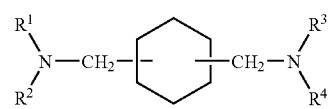

(3)

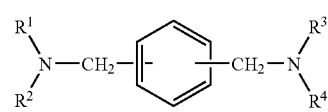

(4)

wherein each of $R^1$, $R^2$, $R^3$ and $R^4$ represents an alkyl group having 1 to 12 carbon atoms, and $R^1$, $R^2$, $R^3$ and $R^4$ may be the same group or different groups and wherein n is an integer of 3 to 15.

11. The water-soluble metal-processing agent according to claim 1, further comprising a mineral oil.

12. The water-soluble metal-processing agent according to claim 1, further comprising a synthetic ester.

13. The water-soluble metal-processing agent according to claim 1, further comprising an antiseptic agent.

\* \* \* \* \*